(12) United States Patent
Sinz

(10) Patent No.: US 9,593,970 B2
(45) Date of Patent: Mar. 14, 2017

(54) LABORATORY SAMPLE DISTRIBUTION SYSTEM AND METHOD FOR CALIBRATING MAGNETIC SENSORS

(71) Applicant: Roche Diagnostics Operations, Inc., Indianapolis, IN (US)

(72) Inventor: Achim Sinz, Waiblingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/840,124

(22) Filed: Aug. 31, 2015

(65) Prior Publication Data

US 2016/0069715 A1 Mar. 10, 2016

(30) Foreign Application Priority Data

Sep. 9, 2014 (EP) .................................. 14184027

(51) Int. Cl.

| | |
|---|---|
| B65G 54/02 | (2006.01) |
| G01D 18/00 | (2006.01) |
| G01D 5/14 | (2006.01) |
| G01N 35/00 | (2006.01) |
| G01R 33/00 | (2006.01) |
| G01N 35/04 | (2006.01) |

(52) U.S. Cl.
CPC ............ *G01D 18/00* (2013.01); *B65G 54/02* (2013.01); *G01D 5/145* (2013.01); *G01N 35/00* (2013.01); *G01N 35/04* (2013.01); *G01R 33/0035* (2013.01); *G01N 2035/0477* (2013.01); *G01N 2035/0493* (2013.01)

(58) Field of Classification Search
CPC .......... G01N 35/04; G01N 2035/0401; G01N 2035/046; G01N 235/0474; G01N 2035/0475; G01N 2035/0489; G01N 35/00; B65G 47/74; B65G 43/00; B65G 35/00; B65G 54/02; G01D 18/00; G01D 5/145

USPC ........................................... 422/63; 198/619
See application file for complete search history.

(56) References Cited

U.S. PATENT DOCUMENTS

| | | |
|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Mark A Deuble
(74) *Attorney, Agent, or Firm* — Roche Diagnostics Operations, Inc.

(57) ABSTRACT

A laboratory sample distribution system comprising a calibration device, a calibration device and a method for calibrating magnetic sensors are disclosed. Magnetic sensors used in a laboratory sample distribution system are calibrated in order to optimize driving of sample container carriers and in order to detect long-term variation in detection characteristics of the magnetic sensors.

14 Claims, 2 Drawing Sheets

(56) References Cited

U.S. PATENT DOCUMENTS

| | | |
|---|---|---|
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,428,957 B2 | 9/2008 | Schaefer |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,281,888 B2 | 10/2012 | Bergmann |
| 8,796,186 B2 | 8/2014 | Shirazi |
| 9,211,543 B2 | 12/2015 | Ohga et al. |
| 9,239,335 B2 | 1/2016 | Heise et al. |
| 2002/0009391 A1 | 1/2002 | Marquiss et al. |
| 2003/0089581 A1 | 5/2003 | Thompson et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1* | 5/2009 | Drenth .................. G01R 33/02 324/207.22 |
| 2009/0142844 A1 | 6/2009 | Le Comte |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0172128 A1 | 7/2011 | Davies et al. |
| 2011/0186406 A1 | 8/2011 | Kraus |
| 2011/0287447 A1 | 11/2011 | Norderhaug et al. |
| 2012/0037696 A1 | 2/2012 | Lavi |
| 2012/0178170 A1* | 7/2012 | Van Praet .................. B01L 9/06 436/47 |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1* | 8/2014 | Heise ..................... G01N 35/04 414/749.2 |
| 2014/0234949 A1 | 8/2014 | Wasson et al. |
| 2015/0014125 A1 | 1/2015 | Hecht |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0276775 A1 | 10/2015 | Mellars et al. |
| 2015/0276776 A1 | 10/2015 | Riether |
| 2015/0276777 A1 | 10/2015 | Riether |
| 2015/0276778 A1 | 10/2015 | Riether |
| 2015/0276781 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |

FOREIGN PATENT DOCUMENTS

| | | |
|---|---|---|
| DE | 3909786 A1 | 9/1990 |
| DE | 102011090044 A1 | 7/2013 |
| EP | 0601213 A1 | 10/1992 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165515 A | 4/1986 |
| GB | 2165516 A | 4/1986 |
| JP | S56-147209 A | 11/1981 |
| JP | 60-223481 A | 11/1985 |
| JP | 61-081323 A | 4/1986 |
| JP | S61-174031 A | 8/1986 |
| JP | S61-094925 A | 9/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | 1148966 A | 6/1989 |
| JP | 01-266860 A | 10/1989 |
| JP | H02-87903 A | 3/1990 |
| JP | 03-192013 A | 8/1991 |
| JP | H05-69350 A | 3/1993 |
| JP | H05-180847 A | 7/1993 |

(56) References Cited

FOREIGN PATENT DOCUMENTS

| | | |
|---|---|---|
| JP | 06-26808 A | 4/1994 |
| JP | 06-148198 A | 5/1994 |
| JP | 6-156730 A | 6/1994 |
| JP | 06-211306 A | 8/1994 |
| JP | 07-228345 A | 8/1995 |
| JP | 07-236838 A | 9/1995 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 3112393 A | 9/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-062188 A | 3/2009 |
| JP | 2009-145188 A | 7/2009 |
| JP | 2009-300402 A | 12/2009 |
| JP | 2013-172009 A | 9/2013 |
| JP | 2013-190400 A | 9/2013 |
| SU | 685591 A1 | 9/1979 |
| WO | 1996/036437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/085670 A1 | 7/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

\* cited by examiner

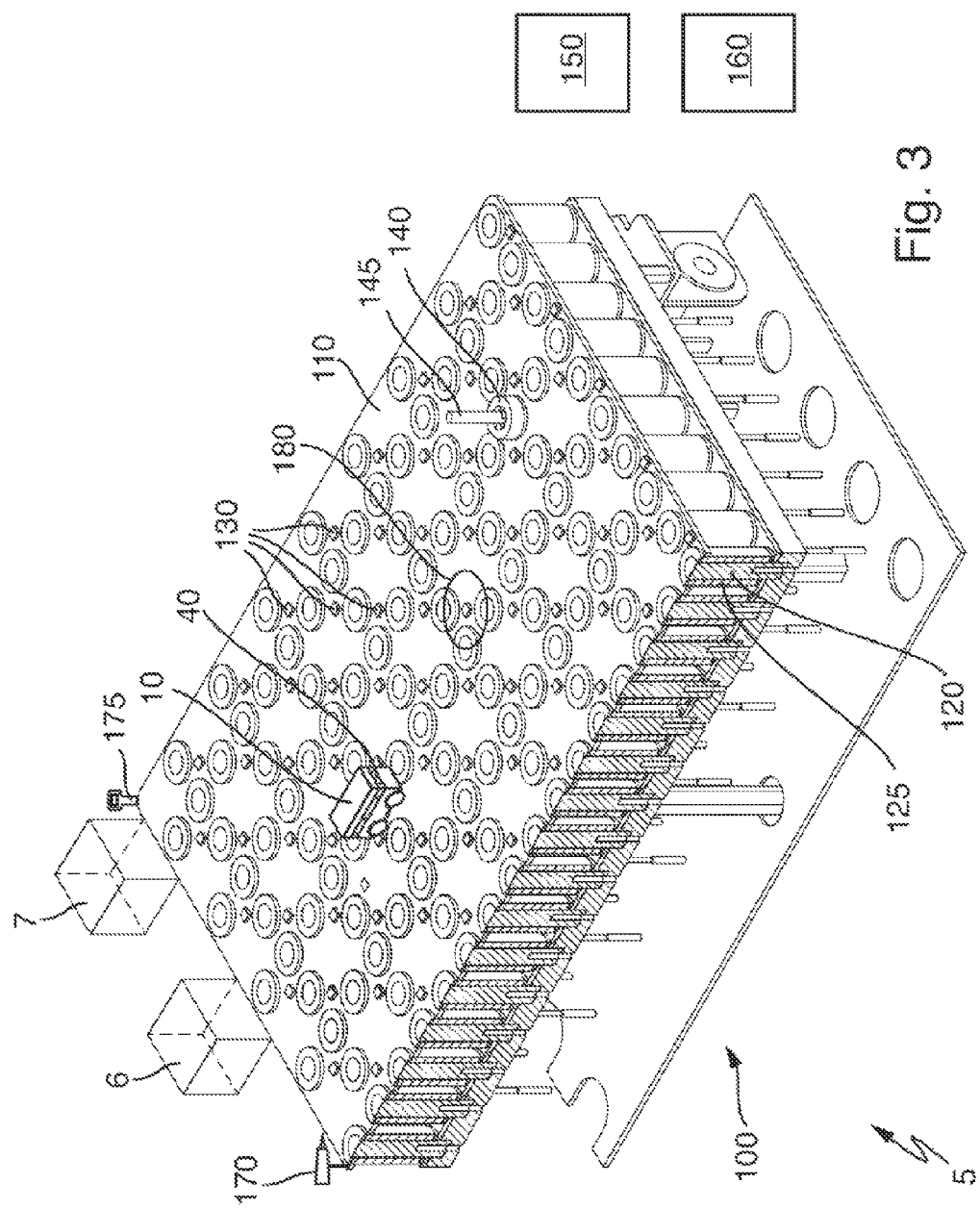

LABORATORY SAMPLE DISTRIBUTION SYSTEM AND METHOD FOR CALIBRATING MAGNETIC SENSORS

CROSS-REFERENCE TO RELATED APPLICATIONS

This application claims priority to EP 14184027.2, filed Sep. 9, 2014, which is hereby incorporated by reference.

BACKGROUND

The present disclosure generally relates to a laboratory sample distribution system and, in particular, to a laboratory sample distribution system and a method for calibrating magnetic sensors.

Laboratory sample distribution systems are used in laboratory automation systems comprising a number of laboratory stations, for example pre-analytical, analytical and/or post-analytical stations. The laboratory sample distribution system can be used in order to distribute sample containers between the laboratory stations and other equipment. The sample containers are typically made of transparent plastic material or glass material and have an opening at an upper side. The sample containers can contain samples such as blood samples or other medical samples.

A typical laboratory sample distribution system discloses sample container carriers that move on a transport plane. A number of electro-magnetic actuators are arranged below the transport plane in order to drive the sample container carriers. In order to detect respective positions of the sample container carriers, a number of magnetic sensors, for example Hall-sensors, are distributed over the transport plane. A position detection of the sample container carriers is critical not only for ensuring that transport tasks are fulfilled correctly, but also for low-level embodiment of drive logic.

However, it has been found that detection characteristics of typical magnetic sensors can vary over time. This leads to decreased performance of the laboratory sample distribution system, for example, due to a less reliable position determination leading to suboptimal driving of the sample container carriers.

Therefore, this is a need for a laboratory sample distribution system and a method for calibrating magnetic sensors to provide for an increased position detecting reliability.

SUMMARY

According to the present disclosure, a laboratory sample distribution system and method are presented. The laboratory sample distribution system can comprise a plurality of sample container carriers. Each sample container carrier can carry one or more sample containers and can comprise at least one magnetically active device. The system can also comprise a transport plane to support the sample container carriers and a plurality of electro-magnetic actuators stationary arranged below the transport plane. The electro-magnetic actuators can move the sample container carriers on top of the transport plane by applying a magnetic force to the sample container carriers. The can further comprise a plurality of magnetic sensors distributed over the transport plane, a control unit to control the movement of the sample container carriers on top of the transport plane using signals provided by the magnetic sensors by driving the electro-magnetic actuators such that the sample container carriers move along corresponding transport paths, and a calibration device. The calibration device can comprises a magnetic calibration element causing a magnetic calibration field and a driver to change a distance between the magnetic calibration element and a magnetic sensor. Additionally, the system can comprise a position determining device to determine the distance between the magnetic calibration element and a respective magnetic sensor and a calibration control unit. The calibration control unit can be configured to monitor signals received from the magnetic sensors while the distance between the magnetic calibration element and a respective magnetic sensor changes. The calibration control unit can be configured to determine magnetic sensor parameters for each of the magnetic sensors in response to the signals received from the magnetic sensors and the determined distance.

Accordingly, it is a feature of the embodiments of the present disclosure to provide a laboratory sample distribution system and a method for calibrating magnetic sensors in order to provide for an increased position detecting reliability. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 3 illustrates a laboratory automation system comprising a laboratory sample distribution system according to an embodiment of the present disclosure.

DETAILED DESCRIPTION

Figure 1:
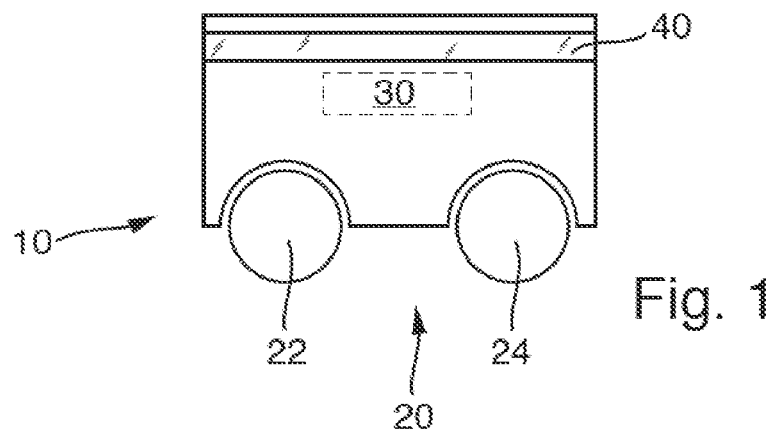
FIG. 1 illustrates a calibration device according to a first embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system is presented The laboratory sample distribution system can comprise a plurality of sample container carriers. Each of sample container carrier can carry one or more sample containers. Each sample container carrier can comprise at least one magnetically active device. Typically, the magnetically active device can be a permanent magnet. The laboratory sample distribution system can further comprise a transport plane to support the sample container carriers.

The laboratory sample distribution system can further comprise a plurality of electro-magnetic actuators stationary arranged below the transport plane. The electro-magnetic actuators can be arranged to move the sample container carriers on top of the transport plane by applying a magnetic force to the sample container carriers.

The laboratory sample distribution system can further comprise a plurality of magnetic sensors distributed over the transport plane. These magnetic sensors can typically be used as position sensors to identify respective positions of the sample container carriers.

The laboratory sample distribution system can further comprise a control unit to control the movement of the sample container carriers on top of the transport plane using signals from the magnetic sensors by driving the electro-magnetic actuators such that the sample container carriers can move along corresponding transport paths.

The laboratory sample distribution system can further comprise a calibration device. The calibration device can comprise a magnetic calibration element causing a defined magnetic calibration field. The calibration device can comprises a driver to change a distance between the magnetic calibration element and a respective magnetic sensor. In order to change a distance between the magnetic calibration element and a respective magnetic sensor, the driver may move the calibration device on the transport plane independently of the electro-magnetic actuators and/or may move the magnetic calibration element in a vertical direction.

The calibration device can be used in order to sense detection behavior of the magnetic sensors as will be explained further below.

The laboratory sample distribution system can further comprise position determining device to determine the actual distance between the magnetic calibration element and a respective magnetic sensor. The position determining device may determine a position of the calibration device on the transport plane independently of the magnetic sensors. It can be noted that the position determining device can be implemented in the calibration device or outside the calibration device. The position determining device can also have components positioned in or at the calibration device and other components positioned outside the calibration device.

The laboratory sample distribution system can further comprise a calibration control unit. The calibration control unit can be identical with the control unit discussed above, but it can also be provided as a separate entity. The calibration control unit may monitor signals received from the magnetic sensors while the distance between the magnetic calibration element and a respective magnetic sensor is changed and may determine one or more magnetic sensor parameters for each of the magnetic sensors in response to the signals received from the magnetic sensors and the determined distance. The magnetic sensor parameters may represent a magnetic detection responsivity of a respective magnetic sensor. In case of magnetic sensors having binary output signals, the magnetic sensor parameters may represent a threshold magnetic field strength defining a change in the binary output signals $0 \rightarrow 1$ or $1 \rightarrow 0$.

The calibration control unit may effect movement of the calibration device on the transport plane using the driver in order to change the distance and may monitor the position of the calibration device using the position determining device. The calibration control unit may further monitor signals received from the magnetic sensors while the calibration device is moving over the transport plane and may determine magnetic sensor parameters for each of the magnetic sensors in response to the signals received from the magnetic sensors and the determined position of the calibration device.

By using the inventive laboratory sample distribution system, it can be possible to detect deviations in detection behavior of the magnetic sensors, e.g. over time. For that purpose, the calibration device and/or the calibration control unit can be implemented as a standard part of the laboratory sample distribution system. According to an alternative embodiment, the calibration device and/or the calibration control unit can be absent in normal operation, but can be brought and operated by a service technician, e.g. when performing regular maintenance.

According to one embodiment, the driver can comprise a number of wheels or chains to move the calibration device on the transport plane. This can allow for an easy and reliable method to transport the calibration device over the transport plane independently of the electro-magnetic actuators. Typically, the electro-magnetic actuators cannot be energized when a measurement by the calibration device is performed, because magnetic fields generated by the electro-magnetic actuators can influence measurements performed by the calibration device.

According to one embodiment, the position determining device can comprise at least one laser emitting device and at least one laser detecting device to determine laser radiation emitted from the laser emitting device. The position determining device can determine the position of the calibration device based on determined laser radiation. Such a position determining device based on laser radiation has been proven as an accurate method for determining the position of the calibration device on the transport plane.

According to one embodiment, the magnetic sensors can deliver a binary presence signal (having exactly two different states) indicative of a magnetic calibration element being present or not present in a specific area covering the magnetic sensor or indicative of a magnetic calibration element being present or not present at a specific distance from the magnetic sensor. The magnetic sensor parameters may e.g. represent geometrical border points of the specific area or the distance.

A calibration device for a laboratory sample distribution system as described above can comprise a magnetic calibration element, causing a magnetic calibration field, and a holder. The holder can support the magnetic calibration element and move the magnetic calibration element in a vertical direction.

The calibration device can provide for an alternative method in order to determine detection behavior of magnetic sensors. By varying a height of the magnetic calibration element, which can be accomplished by moving the magnetic calibration element in a vertical direction, a resulting magnetic field at a magnetic sensor can depend on a vertical position and the magnetic calibration field. For example, a field at a specific sensor can be lowered by moving the magnetic calibration element upwards. This can omit the need for accurate x-y-position determining device because the calibration device can be left at one place during the measurement.

According to one embodiment, the holder can move the magnetic calibration element in the vertical direction responsive to a signal received from a control unit of the sample distribution system. This can allow for a remote control of a calibration process by the control unit. The control unit can drive the calibration device over the transport plane using the electro-magnetic actuators. If the calibration device has reached a specific position, the control unit can instruct the holder to alter the height of the magnetic calibration element.

According to one embodiment, the calibration device can comprise a driver to move the calibration device over the transport plane. This can allow for an autonomous movement of the calibration device over the transport plane. Such a driver can, for example, comprise a plurality of wheels or chains to move the calibration device on the transport plane. Alternatively, the magnetic calibration element can be used in order to allow for a driving of the calibration device over the transport plane similar to sample container carriers.

With the calibration control unit just described, an automatic calibration of magnetic sensors can be performed. Especially, the calibration device can be driven from sensor to sensor and the process of vertical movement can be performed over/for each sensor. This can allow for a complete calibration of all sensors distributed over the transport plane even during normal operation mode.

According to one embodiment, the magnetic sensors can be Hall-sensors. This embodiment can be used for all kinds of laboratory sample distribution systems as discussed above.

A method for calibrating magnetic sensors of a laboratory sample distribution system as described above is also presented The method can comprises: providing the calibration device on the transport plane, changing a distance (and further parameters, e.g. an angle between the magnetic calibration element and the respective magnetic sensor and the like, if necessary) between the magnetic calibration element and a respective magnetic sensor, determining the distance (and further parameters, e.g. the angle between the magnetic calibration element and the respective magnetic sensor, and the like, if necessary) between the magnetic calibration element and the respective magnetic sensor, monitoring a signal received from the respective magnetic sensor while the distance between the magnetic calibration element and the respective magnetic sensor is changed, and determining magnetic sensor parameters for the respective magnetic sensor in response to the signals received from the respective magnetic sensor and the determined distance.

According to one embodiment, the method can further comprise updating calibration data based on monitoring of magnetic sensors and/or determination of border points.

The presented disclosure provides for the possibility to update calibration data in form of magnetic sensor parameters based on measurements performed. For example, a database storing such magnetic sensor parameters can be updated. The database can deliver data that can be used in order to optimize driving algorithms or other embodiments used for every-day operation. In addition, the database may be evaluated in order to detect long-term variations in detection behavior of magnetic sensors. The data can, for example, also be used in order to determine a need for replacement of the sensors and to detect defect sensors.

Referring initially to FIG. 1, FIG. 1 shows a calibration device 10 according to a first embodiment. The calibration device 10 can comprise a driver 20 to move the calibration device 10 on a transport plane of a laboratory sample distribution system as will be described further below. The driver 20 can comprise a first wheel 22, a second wheel 24 and additionally two corresponding wheels on the other side of the calibration device 10 that are not visible in FIG. 1. Velocity and direction of movement can be controlled by motors and by tilting two of the wheels, not shown in FIG. 1 for reasons of simplicity.

The calibration device 10 can further comprise a magnetic calibration element in the form of a permanent magnet 30. The magnetic calibration element 30 can be positioned at a specific height above a surface on which the calibration device 10 is moving and an cause a defined magnetic field. Thus, the magnetic calibration element 30 can induce a defined magnetic field on a sensor that can be positioned below the calibration device 10.

The calibration device 10 can further comprises an optical mirror 40 that can be used to determine the position of the calibration device 10, as will be described further below.

Figure 2:
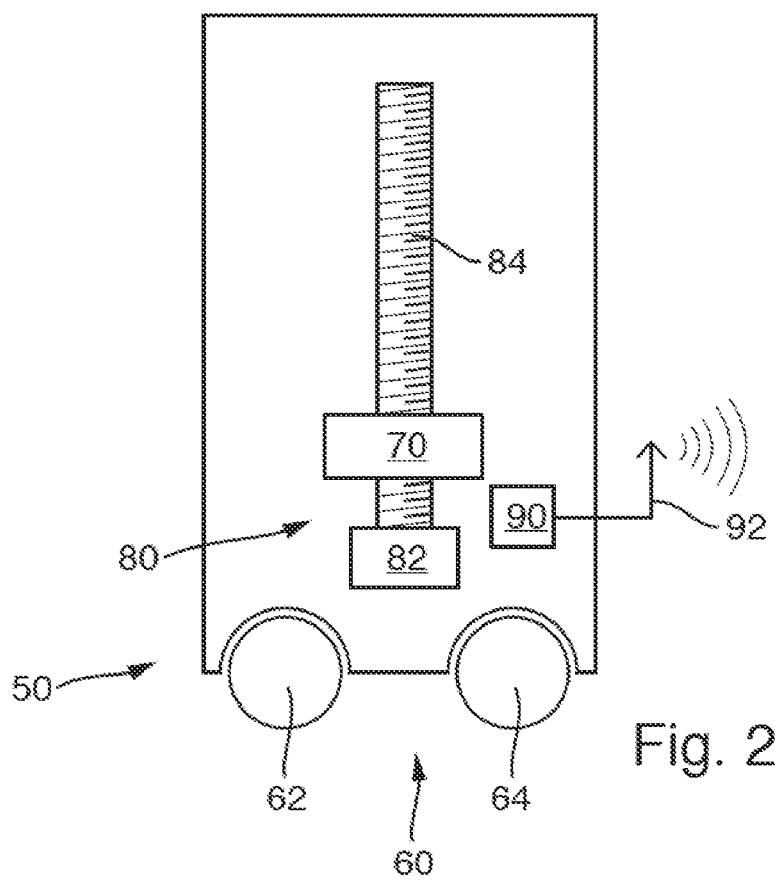
FIG. 2 illustrates a calibration device according to a second embodiment of the present disclosure.

FIG. 2 shows a calibration device 50 according to a further embodiment in a highly schematic cross-sectional view. The calibration device 50 can comprise a driver 60 to move the calibration device 10 on a transport plane of a laboratory sample distribution system as will described further below. The driver 60 can comprise a first wheel 62, a second wheel 64 and additionally two corresponding wheels on the other side of the calibration device 10 that are not visible in FIG. 2. Velocity and direction of movement can be controlled by motors and by tilting two of the wheels, not shown in FIG. 2 for reasons of simplicity.

The calibration device 50 can further comprise a magnetic calibration element in the form of a permanent magnet 70. The magnetic calibration element 70 can induce a specified, known magnetic field. In contrast to the permanent magnet 30 of the calibration device 10 according to the first embodiment, the permanent magnet 70 can be moved vertically inside the calibration device 50.

For that purpose, the calibration device 50 can comprises a holder 80. The holder 80 can comprise an electric motor 82 and a threaded bar 84. The threaded bar 84 can extend through the magnetic calibration element 70. The magnetic calibration element 70 can be secured against rotation. Thus, it can be possible to move the magnetic calibration element 70 up and down by rotating the threaded bar 84 using the electric motor 82. Thus, a magnetic field strength of the magnetic field induced by the magnetic calibration element 70 at a magnetic sensor positioned below the calibration device 50 can be adjusted by moving the permanent magnet 70 up and down.

The calibration device 50 can comprise position determining device to determine the vertical position of the magnetic calibration element 70 relative to the transport plane. If the vertical position of the magnetic calibration element 70 is known, the distance between the magnetic calibration element 70 and a respective magnetic sensor 130 can be calculated, provided that the x-y-position of the calibration device 50 on the transport plane is known.

The calibration device 50 can comprise a control device 90 having an antenna 92. The control device 90 can communicate with a control unit of a laboratory sample distribution system or with a calibration control unit of such a laboratory sample distribution system. The control device 90 can receive instructions from the control unit or the calibration control unit indicating that the permanent magnet 70 can be moved up and down. The control device 90 can drive the electric motor 82 accordingly, so that such instructions can be fulfilled.

The control device 90 can receive drive commands via the antenna 92, indicating that the calibration device 50 can move using its driver 60. Thus, the calibration device 50 can be used in order to move over a transport plane of a laboratory sample distribution system and to stop over each sensor to be calibrated. The magnetic calibration element 70 can then be moved up and down in order to calibrate the sensor. As the magnetic field strength at the magnetic sensor is known dependent of the height or distance from the magnetic sensor, magnetic sensor parameters in the form of measurement characteristics of the magnetic sensor can be determined depending on the known field strength.

FIG. 3 shows a laboratory automation system 5 comprising a first laboratory station 6, a second laboratory station 7 and a laboratory sample distribution system 100. The first laboratory station 6 and the second laboratory station 7 are shown exemplarily for a plurality of laboratory stations that are typically comprised by a laboratory automation system. Such laboratory stations can, for example, be pre-analytical, analytical and/or post-analytical stations. They can, for example, perform tasks like analyzing a sample, centrifugation of a sample, and the like.

The laboratory sample distribution system 100 can comprise a transport plane 110, under which a plurality of electro-magnetic actuators 120 can be arranged. Each electro-magnetic actuator 120 can have a corresponding ferromagnetic magnetic core 125.

A plurality of magnetic sensors 130, implemented as Hall-sensors, can be distributed over the transport plane 110.

The laboratory sample distribution system 100 can further comprise a plurality of sample container carriers 140, wherein only one exemplary sample container carrier 140 is shown in FIG. 3. The sample container carrier 140 can carry a sample container 145 that is embodied as a tube.

The laboratory sample distribution system 100 can further comprise a control unit 150 to drive the electro-magnetic actuators 120 such that the sample container carriers 140 can move along respective transport paths. For that purpose, each sample container carrier 140 can comprise a magnetically active device embodied as a permanent magnet. Those permanent magnets are not shown in FIG. 3, because they are contained inside the sample container carriers 140.

The control unit 150 can receive signals from the magnetic sensors 130 to determine the position of a sample container carrier 140 on the transport plane. The magnetic sensors 130 can sense a magnetic field generated by the permanent magnet positioned inside the sample container carrier 140. The control unit 150 can control the movement of the sample container carrier 140 on top of the transport plane 110 using the signals provided by the magnetic sensors 130.

The laboratory sample distribution system 100 can further comprise a calibration control unit 160 and a calibration device 10. The calibration device 10 is embodied as shown in FIG. 1 and as described with respect to this figure.

The calibration device 10 can move over the transport plane 110 autonomously using its driver 20.

The laboratory sample distribution system 100 can further comprise a laser emitting device 170 and a laser detection device 175. The laser emitting device 170 and the laser detection device 175 together with the mirror 40 comprised by the calibration device 10 can form a position determining device. The position determining device can sense the position of the calibration device 10 with high accuracy by emitting a laser beam on the mirror 40 that can be reflected by the mirror and detected by the laser detection device 175.

While the calibration device 10 is moving over the transport plane 110, the calibration control device 160 can monitor signals from the magnetic sensors 130. In addition, it can receive position information from the position determining device 40, 170, 175. Thus, the calibration control device 160 can be aware of a magnetic field at each of the magnetic sensors 130 when the calibration device 10 is moving over it.

This data can be used in order to determine magnetic sensor parameters for each of the magnetic sensors 130 in response to the signals received from the magnetic sensors 130 and the determined position. This calibration data can be used in order to update a calibration database. By using the calibration database, the control unit 150 can optimize its driving of the electromagnetic actuators 120 in order to move the sample container carriers 140.

The magnetic sensor parameters can be used in order to detect defect magnetic sensors 130 and in order to detect long-term variations of the detection characteristics of the magnetic sensors 130.

It should be noted that the magnetic sensors 130 can be implemented in at least two ways. In a first embodiment, each magnetic sensor can deliver an analog signal representative for the magnetic field strength currently measured by the magnetic sensor. In a second embodiment, each magnetic sensor can output a signal having exactly two states (i.e. a binary signal), indicating if a magnetic element, e.g. the magnetically active device of the sample container carrier 140, is present or not present in a specific area or volume around the magnetic sensor 130 or distance from the magnetic sensor 130.

Such an area 180 is shown exemplarily for one of the magnetic sensors 130 in FIG. 3. In this embodiment, the calibration control unit 160 may determine border points of the respective area 180. Such border points can be indicative for the extension of the area 180 and can, for example, be tracked over time.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the laboratory sample distribution system comprising:
a plurality of sample container carriers, wherein each sample container carrier carries one or more sample containers and comprises at least one magnetically active device;
a transport plane to support the sample container carriers;
a plurality of electro-magnetic actuators stationary arranged below the transport plane, wherein the electro-magnetic actuators move the sample container carriers on top of the transport plane by applying a magnetic force to the sample container carriers;
a plurality of magnetic sensors distributed over the transport plane;
a control unit to control the movement of the sample container carriers on top of the transport plane using signals provided by the magnetic sensors by driving the electro-magnetic actuators such that the sample container carriers move along corresponding transport paths;
a calibration device, wherein the calibration device comprises,
a magnetic calibration element causing a magnetic calibration field, and
a driver to change a distance between the magnetic calibration element and a magnetic sensor;
a position determining device to determine the distance between the magnetic calibration element and a respective magnetic sensor; and
a calibration control unit, wherein the calibration control unit is configured to monitor signals received from the magnetic sensors while the distance between the magnetic calibration element and a respective magnetic sensor changes, and wherein the calibration control unit is configured to determine magnetic sensor parameters for each of the magnetic sensors in response to the signals received from the magnetic sensors and the determined distance.

2. The laboratory sample distribution system according to claim 1, wherein the driver moves the calibration device on the transport plane independently of the electro-magnetic actuators.

3. The laboratory sample distribution system according to claim 1, the position determining device determines a position of the calibration device on the transport plane independently of the magnetic sensors.

4. The laboratory sample distribution system according to claim 3, wherein the position determining device comprises at least one laser emitting device and at least one laser detecting device adapted to determine laser radiation emitted from the laser emitting device.

5. The laboratory sample distribution system according to claim 4, wherein the position determining device determines the position of the calibration device based on the determined laser radiation.

6. The laboratory sample distribution system according to claim 1, wherein the calibration control unit is configured to effect movement of the calibration device on the transport plane and to monitor the position of the calibration device using the position determining device.

7. The laboratory sample distribution system according to claim 1, wherein the calibration control unit is configured to monitor signals received from the magnetic sensors while the calibration device is moving over the transport plane and is configured to determine the magnetic sensor parameters for each of the magnetic sensors in response to the signals received from the magnetic sensors and the determined position of the calibration device.

8. The laboratory sample distribution system according to claim 1, wherein each of the magnetic sensors is configured to deliver a presence signal, if the magnetic calibration element is present within a specific area covering the magnetic sensor and/or within a specific vertical distance from the magnetic sensor.

9. The laboratory sample distribution system according to claim 8, wherein the calibration control unit is configured to determine the magnetic sensor parameters for each of the magnetic sensors in response to the presence signals and the determined distance.

10. The laboratory sample distribution system according to claim 1, wherein the calibration device comprises a holder to support the magnetic calibration element and to move the magnetic calibration element in a vertical direction.

11. The laboratory sample distribution system according to claim 10, wherein the holder moves the magnetic calibration element in the vertical direction responsive to a signal received from the calibration control unit.

12. The laboratory sample distribution system according to claim 1, wherein the magnetic sensors are Hall-sensors.

13. The laboratory sample distribution system according to claim 1, wherein the control unit controls the movement of the sample container carriers on top of the transport plane using the signals provided by the magnetic sensors and using the magnetic sensor parameters.

14. A method for calibrating magnetic sensors of a sample distribution system according to claim 1, the method comprising:
   providing the calibration device on the transport plane;
   changing a distance between the magnetic calibration element and a respective magnetic sensor;
   determining the distance between the magnetic calibration element and the respective magnetic sensor;
   monitoring a signal received from the respective magnetic sensor while the distance between the magnetic calibration element and the respective magnetic sensor changes; and
   determining magnetic sensor parameters for the respective magnetic sensor in response to the signals received from the respective magnetic sensor and the determined distance.

* * * * *